United States Patent
Granier et al.

(10) Patent No.: US 7,812,195 B2
(45) Date of Patent: Oct. 12, 2010

(54) CYCLOHEXENYL BUTENONES AND FRAGRANCE COMPOSITIONS COMPRISING THEM

(75) Inventors: Thierry Granier, Duebendorf (CH); Andreas Hart, Uster (CH); Jerzy A. Bajgrowicz, Zurich (CH)

(73) Assignee: Givaudan SA, Vernier (CH)

( * ) Notice: Subject to any disclaimer, the term of this patent is extended or adjusted under 35 U.S.C. 154(b) by 0 days.

(21) Appl. No.: 12/518,591

(22) PCT Filed: Dec. 11, 2007

(86) PCT No.: PCT/CH2007/000626

§ 371 (c)(1), (2), (4) Date: Jun. 10, 2009

(87) PCT Pub. No.: WO2008/071026

PCT Pub. Date: Jun. 19, 2008

(65) Prior Publication Data

US 2010/0016197 A1    Jan. 21, 2010

(30) Foreign Application Priority Data

Dec. 13, 2006    (GB) ................. 0624814.0

(51) Int. Cl.
C07C 49/543    (2006.01)
(52) U.S. Cl. ............... 568/377; 512/24; 510/106
(58) Field of Classification Search ............. 568/377; 512/24; 510/106
See application file for complete search history.

(56) References Cited

U.S. PATENT DOCUMENTS

| | | | |
|---|---|---|---|
| 3,890,370 A * | 6/1975 | Buchi et al. ........... | 560/128 |
| 4,311,754 A * | 1/1982 | Trenkle et al. .......... | 442/102 |
| 4,392,993 A | 7/1983 | Thomas et al. | |
| 4,460,792 A * | 7/1984 | Schulte-Elte et al. ...... | 568/341 |
| 4,512,928 A * | 4/1985 | Sugerman et al. ........ | 560/234 |
| 4,704,477 A | 11/1987 | Gebauer et al. | |
| 2006/0211889 A1 | 9/2006 | Jacoby et al. | |

FOREIGN PATENT DOCUMENTS

| | | |
|---|---|---|
| EP | 0093840 A | 11/1983 |
| EP | 0199330 A | 10/1986 |
| EP | 0231556 A | 8/1987 |
| JP | 59001462 A | 1/1984 |

OTHER PUBLICATIONS

English Language abstract for JP59001462 taken from esp@cenet. com, 1984.
English Language abstract for EP0093840 taken from esp@cenet. com, Nov. 1983.
Rose Ketones: Celebrating 30 Years of Success, Alvin Williams, Perfumer & Flavorist, vol. 27, Mar./Apr. 2002, p. 18-31.
The Preparation of δ-Damascone and its Analogues, and Their Odour (with English Language Translation).

* cited by examiner

*Primary Examiner*—John R Hardee
(74) *Attorney, Agent, or Firm*—Norris McLaughlin & Marcus, PA

(57) ABSTRACT

The present invention relates to substituted cyclohexenyl butenones of the formula

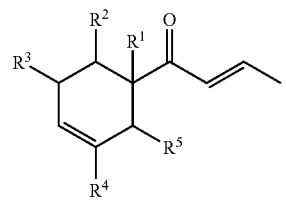

wherein $R^1$, $R^2$, $R^3$, $R^4$ and $R^5$ are independently selected from hydrogen, methyl or ethyl; and the total sum of carbon atoms is 11 to 15; as well as to a method for their production and to fragrance compositions and fragrance applications comprising them.

15 Claims, No Drawings

CYCLOHEXENYL BUTENONES AND FRAGRANCE COMPOSITIONS COMPRISING THEM

This is an application filed under 35 USC 371 of PCT/CH2007/000626.

The present invention refers to a novel class of substituted cyclohexenyl butenones having damascone-like odour notes, and to their use as odorants. This invention relates furthermore to a method for their production and to fragrance compositions comprising them.

In the fragrance industry there is a constant demand for new compounds that enhance, modify or improve on odour notes. Damascones, also known as rose ketones, constitute an important class of perfume ingredients. They display particular floral (rosy)-fruity notes reminiscent of dried fruits. Thus, there is a constant desire to find new compounds possessing a damascone-like odour note.

The α-, β-, δ-damascones (A) and β-damascenone (C) can be considered as a subfamily in the floral-fruity domain of perfumery ingredients, as they display a very typical and complex odour of rose and fruit (such as apple or plum with blackcurrant aspects). Thus, while the scent of α-damascone is rose, apple, blackcurrant, the odour of β-damascone is more blackcurrant, plum, and still rose. The olfactive notes of δ-damascone are more red rose and less apple than α-damascone and less plum than β-damascone, whereas β-damascenone is olfactorily described as rose, plum, raspberry, sugary (A. Williams; Perfumer & Flavorist 2002, 27, 18-31).

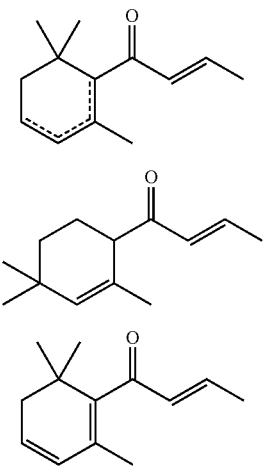

A large number of cyclohexenylbutenones has been described in literature as damascone analogues. However, the geminal methyl groups of the cyclohexene ring of the damascones are usually retained. For example, isodamascone (B), possessing natural fruit-like and increasing wine-like and fresh flower-like nuances (U.S. Pat. No. 3,822,315), or γ-damascone, which is more fruity than α- and β-damascone with a dominant floral rosy green note (A. Williams; Perfumer & Flavorist 2002, 27, 18-31). Indeed, the structural analogues of δ-damascone not possessing a gem-dimethyl group on the cyclohexene ring display odor notes that are very distinguishable from the typical damascone note. For example, 1-(1,3/4-dimethyl-cyclohex-3-en-1-yl)but-2-en-1-ones (D), disclosed in U.S. Pat. No. 4,392,993, bringing "medicinal-type" odor note to shampoos, are described as fruity but reminiscent of melon, while their flowery note is reminiscent of camomile and the aromatic note is herbaceous, thujone-like. The 1-(1,2,4,6-tetramethyl cyclohex-3-en-1-yl) but-2-en-1-one (E) is described as being woody-turpentine and vegetable (Andreev, V. M.; Andreeva, L. K.; Ratnikova, E. V.; Fomchenko, Z. V.; Grigor'eva, L. T. Gidrolíznaya i Lesokhimicheskaya Promyshlennost, 1993, 1, 23-4). Or the butenones of formula F, wherein R is hydrogen or methyl, which are disclosed in JP-A-59-146, are simply described as having flower-like or fruit-like smell without any mention of an olfactory analogy with the typical odour note of the damascones.

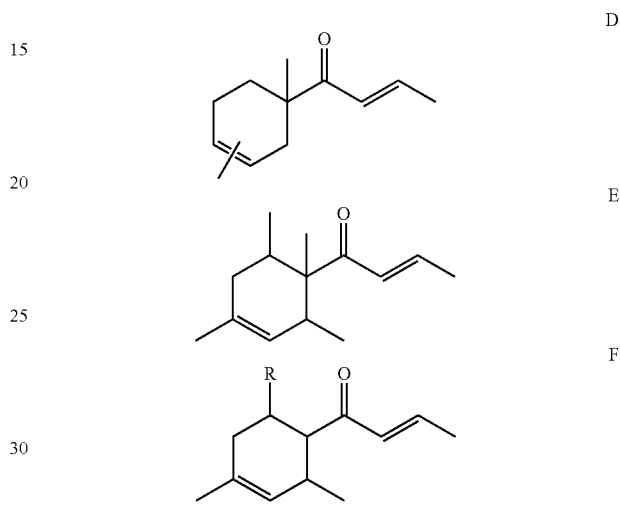

Accordingly, everything in the prior art indicates that the geminal methyl groups are an important structural feature of the compounds in order to retain the typical odour note of damascone.

Surprisingly, we have found that the presence of the geminal methyl groups on the cyclohexene ring is in some cases not necessary for the obtaining of strong dried-fruit odour notes, very similar to the odour note of the damascones.

Thus, the present invention refers in one of its aspects to a compound of formula (I)

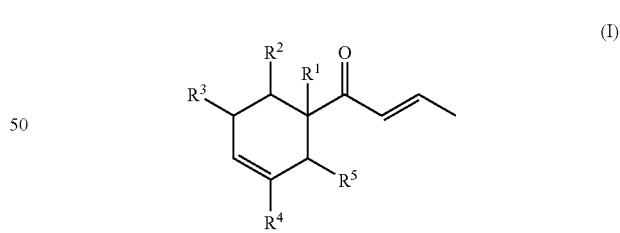

wherein
the double bound in the side chain is in E-configuration;
$R^1$, $R^2$, $R^3$, $R^4$ and $R^5$ are independently selected from hydrogen, methyl or ethyl; and
the total sum of carbon atoms is 11 to 15, preferably 11 to 14, e.g. 12 or 13;
with the proviso that
if $R^2$ is hydrogen then $R^5$ is methyl or ethyl;
if $R^5$ is hydrogen then $R^2$ is methyl or ethyl; and
if $R^4$ is methyl or ethyl then $R^5$ is methyl or ethyl.

In particular embodiments are compounds of formula (I) wherein i) $R^1$ is hydrogen, methyl or ethyl, $R^2$ is methyl or ethyl, and $R^3$, $R^4$ and $R^5$ are hydrogen;
ii) $R^1$ and $R^2$ are independently selected from hydrogen, methyl or ethyl, $R^3$ and $R^4$ are hydrogen and $R^5$ is methyl or ethyl;
iii) $R^1$ is selected from hydrogen, methyl or ethyl, $R^2$ is methyl or ethyl, $R^3$ is methyl or ethyl, and $R^4$ and $R^5$ are hydrogen;
iv) $R^1$ and $R^2$ are independently selected from hydrogen, methyl or ethyl, $R^4$ and $R^5$ are independently selected from methyl or ethyl, and $R^3$ is hydrogen;
v) $R^1$ and $R^2$ are independently selected from hydrogen, methyl or ethyl, $R^4$ is hydrogen and $R^3$ and $R^5$ are independently selected from methyl or ethyl; or
vi) $R^1$ and $R^2$ are independently selected from hydrogen, methyl or ethyl, $R^3$, $R^4$ and $R^5$ are independently selected from methyl or ethyl.

The compounds of formula (I) comprise up to four chiral centres and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or stereoselective synthesis.

Compounds of formula (I) wherein at least one of the residues $R^2$, $R^3$, $R^4$ and $R^5$ is ethyl are of particular interest.

Particularly preferred compounds of formula (I) are
(2E)-1-(6-ethyl-2-methylcyclohex-3-enyl)but-2-en-1-one,
(2E)-1-(2-ethyl-6-methylcyclohex-3-enyl)but-2-en-1-one,
(2E)-1-(6-ethylcyclohex-3-enyl)but-2-en-1-one,
(2E)-1-(1,2,5,6-tetramethylcyclohex-3-enyl)but-2-en-1-one,
(2E)-1-(1,2-dimethylcyclohex-3-enyl)but-2-en-1-one,
(2E)-1-(2,5-dimethylcyclohex-3-enyl)but-2-en-1-one,
(2E)-1-(1,6-dimethyl-2-ethylcyclohex-3-enyl)but-2-en-1-one,
(2E)-1-(2,5-dimethyl-6-ethylcyclohex-3-en)but-2-en-1-one,
(2E)-1-(2,3-dimethyl-6-ethylcyclohex-3-enyl)but-2-en-1-one,
(2E)-1-(2,3,6-trimethylcyclohex-3-enyl)but-2-en-1-one,
(2E)-1-(2,3,5,6-tetramethylcyclohex-3-enyl)but-2-en-1-one,
(2E)-1-(2,5,6-trimethylcyclohex-3-enyl)but-2-en-1-one,
(2E)-1-(1,2,3-trimethylcyclohex-3-enyl)but-2-en-1-one,
(2E)-1-(1,2,3,5-tetramethylcyclohex-3-enyl)but-2-en-1-one,
(2E)-1-(1,2,3,6-tetramethylcyclohex-3-enyl)but-2-en-1-one,
(2E)-1-(2,3-dimethylcyclohex-3-enyl)but-2-en-1-one,
(2E)-1-(2,3,5-trimethylcyclohex-3-enyl)but-2-en-1-one,
(2E)-1-(1,2,6-trimethylcyclohex-3-enyl)but-2-en-1-one,
(2E)-1-(1,2,5-trimethylcyclohex-3-enyl)but-2-en-1-one, and
(2E)-1-(1,6-dimethylcyclohex-3-enyl)but-2-en-1-one.

Among these compounds, for example (2E)-1-(6-ethyl-2-methylcyclohex-3-enyl)but-2-en-1-one was found to have an odour that was cleaner and had less of a cork-aspect when compared to 6-damascone both when smelled alone on blotter and in formula, i.e. when combined with other fragrance ingredients.

The compounds according to the present invention may be used alone or in combination with known odorant molecules selected from the extensive range of natural and synthetic molecules currently available, such as ethereal oils and extracts, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

The following list comprises examples of known odorant molecules, which may be combined with the compounds of the present invention:

ethereal oils and extracts, e.g. oak moss absolute, basil oil, tropical fruit oils, such as bergamot oil and mandarine oil, mastic absolute, myrtle oil, palmarosa oil, patchouli oil, petitgrain oil, wormwood oil, lavender oil, rose oil, jasmin oil, ylang-ylang oil and sandalwood oil.

alcohols, e.g. cis-3-hexenol, cinnamic alcohol, citronellol, Ebanol®, eugenol, farnesol, geraniol, menthol, nerol, rhodinol, Super Muguet™, linalool, phenylethyl alcohol, Sandalore®, terpineol and Timberol® (1-(2,2,6-Trimethylcyclohexyl)hexan-3-01).

aldehydes and ketones, e.g. citral, hydroxycitronellal, Lilial®, methylnonylacetaldehyde, anisaldehyde, allylionone, verbenone, nootkatone, geranylacetone, α-amylcinnamic aldehyde, Georgywood™, hydroxycitronellal, Iso E Super®, Isoraldeine® (methylionone), Hedione®, maltol, methyl cedryl ketone, and vanillin.

ethers and acetals, e.g. Ambrox®, geranyl methyl ether, rose oxide or Spirambrene®.

esters and lactones, e.g. benzyl acetate, cedryl actetate, γ-decalactone, Helvetolide®, γ-undecalactone, vetivenyl acetate, cinnamyl propionate, citronellyl acetate, decyl acetate, dimethylbenzylcarbinyl acetate, ethyl acetoacetate, ethyl acetylacetate, cis-3-hexenyl isobutyrate, linalyl acetate and geranyl acetate.

macrocycles, e.g. ambrettolide, ethylene brassylate or Exaltolide®.

heterocycles, e.g. isobutylchinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odorant ingredients. The proportion is typically from 0.0001 to 2 weight percent of the application. In one embodiment, compounds of the present invention may be employed in a fabric softener in an amount of from 0.0001 to 0.005 weight percent. In another embodiment, compounds of the present invention may be used in an alcoholic solution in amounts of from 0.01 to 3 weight percent, more preferably between 0.5 and 2 weight percent. However, these values are given only by way of example, since the experienced perfumer may also achieve effects or may create novel accords with lower or higher concentrations, e.g. up to about 20 weight percent based on the fragrance composition.

The compounds of the present invention may be employed into the fragrance application simply by directly mixing the fragrance composition with the fragrance application, or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application and consumer products resulting therefrom. The method comprises the incorporation therein of a compound of formula (I) as a fragrance ingredient, either by directly admixing the compound to the application or by admixing a fragrance composition comprising a compound of formula (I), which may then be mixed to a fragrance application, using conventional techniques and methods. Through the addition of an olfactory acceptable amount of a compound of the present invention, the odor notes of a fragrance application will be improved, enhanced or modified.

Thus, the invention furthermore provides a method for improving, enhancing or modifying a fragrance application through the addition thereto of an olfactory acceptable amount of a compound of formula (I), or a mixture thereof.

The invention also provides a fragrance application comprising:
a) as odorant a compound of formula (I) or a mixture thereof; and
b) a consumer product base.

As used herein, "fragrance application" means any products, such as fine fragrances, e.g. eaux de perfume and eaux de toilette; household products, e.g. detergents for dishwasher, surface cleaner, air freshener; laundry products, e.g. softener, bleach, detergent; body care products, e.g. after-shave lotion, shampoo, shower gel, shower and bath salt, hygiene product; and cosmetics, e.g. deodorants, vanishing creams, comprising an odorant. This list of products is given by way of illustration and is not to be regarded as being in any way limiting.

Compounds of formula (I) may be prepared by Diels-Alder cycloaddition followed by aldol condensation with acetaldehyde and water elimination under conditions known in the art.

The invention is now further described with reference to the following non-limiting examples. These examples are for the purpose of illustration only and it is understood that variations and modifications can be made by one skilled in the art.

EXAMPLE 1

(2E)-1-(rel-(1R,2S,6S)-6-Ethyl-2-methylcyclohex-3-enyl)but-2-en-1-one

A) At −15° C., a solution of $BF_3.OEt_2$ (54 g, 0.38 mol) in dichloromethane (680 ml) was treated within 10 min. with 3-hexen-2-one (220.1 g, 89% pure, 2 mol). 1,3-Pentadiene (490 g, 7.2 mol, precooled at 0° C.) was then added and the resulting solution stirred 30 min. at 0° C. then 1 h at 20° C. before being cooled at 0° C. and treated with a solution of 20% aqueous $K_2CO_3$ (250 ml). The resulting mixture was stirred 40 min. and concentrated (43° C. till 300 mbar). The aqueous phase was washed with hexane (500 ml) and the combined organic phases with 20% aqueous $K_2CO_3$ (100 ml), three times with saturated aqueous NaCl solution, dried ($MgSO_4$) and concentrated. Sulzer-distillation (0.4-0.1 mbar) of the crude product (400 g) gave 1-(rel-(1R,2S,6S)-6-ethyl-2-methylcyclohex-3-enyl)ethan-1-one (326 g, 98% yield).

Boiling point: 45° C. (0.1 mbar).

$^1$H-NMR (400 MHz, $CDCl_3$): δ5.70-5.59 (m, H—C(3'), H—C(4')), 2.72 (dd, J=5.3, 10.6, H—C(1')), 2.57-2.48 (m, H—C(2')), 2.25-2.17 (m, H—C(5')), 2.15 (s, MeCO), 1.96-1.85 (m, H—C(6')), 1.73-1.62 (m, H—C(5')), 1.62-1.51 (m, C(6')CHMe), 1.16-1.03 (m, C(6')CHMe), 0.86 (t, J=7.3, MeCH$_2$), 0.85 (d, J=7.1, MeC(2')).

$^{13}$C-NMR (100 MHz, $CDCl_3$): δ210.73 (s, CO), 131.21 (d, C(3')), 125.19 (d, C(4')), 55.61 (d, C(1')), 30.76 (q, C(2)), 30.67 (d, C(2')), 30.33 (d, C(6')), 29.71 (t, C(5')), 26.33 (t, CH$_2$Me)), 16.95 (q, MeC(2')), 10.68 (q, CH$_2$Me).

MS (EI): 166 (14), 151 (7), 137 (30), 123 (64), 108 (11), 95 (23), 94 (14), 93 (39), 91 (17), 81 (100), 79 (32), 77 (25), 67 (33), 55 (26), 43 (98), 41 (26), 39 (20).

B) At −78° C., a solution of diisopropylamine (6.6 g, 34 mmol) in tetrahydrofuran (23 ml) was treated with n-butyl lithium (21 ml, 1.6M in hexane, 34 mmol). The resulting solution was warmed to 0° C., cooled to −78° C., and treated with a solution of 1-(rel-(1R,2S,6S)-6-ethyl-2-methylcyclohex-3-enyl)ethan-1-one (4.5 g, 27 mmol) in tetrahydrofuran (23 ml). The resulting solution was stirred 20 min. at −20° C., cooled to −78° C. and treated with a solution of acetaldehyde (1.8 g, 41 mmol) in tetrahydrofuran (23 ml). After 1 h stirring, aqueous 1 N HCl (50 ml) was added and the reaction mixture warmed to 20° C. The aq. phase was extracted with diethyl ether and the combined org. phases dried ($MgSO_4$), and concentrated. A solution of the residue (4.9 g) in toluene (4.9 ml) was treated with para-toluene sulfonic acid monohydrate (20 mg) and refluxed overnight. The reaction mixture was cooled, treated with a saturated aqueous solution of $NaHCO_3$ and the aqueous phase was extracted with diethyl ether. The combined organic phases were dried ($MgSO_4$) and concentrated. FC (550 g $SiO_2$, hexane/diethyl ether 9:1) of the crude product gave (2E)-1-(rel-(1R,2S,6S)-6-ethyl-2-methylcyclohex-3-enyl)but-2-en-1-one (2.9 g, 56%).

Boiling point: 96° C. (0.7 mbar).

$^1$H-NMR (400 MHz, $CDCl_3$): δ6.87 (dq, J=6.8, 15.7, H—C(3)), 6.16 (dq, J=1.7, 15.7, H—C(2)), 5.70-5.60 (m, H—C(3'), H—C(4')), 2.89 (dd, J=5.4, 10.7, H—C(1')), 2.52-2.41 (m, H—C(2')), 2.27-2.18 (m, H—C(5')), 2.03-1.93 (m, H—C(6')), 1.90 (dd, J=1.8, 6.8, MeC(3)), 1.74-1.65 (m, H—C(5')), 1.61-1.50 (m, C(6')CHMe), 1.16-1.03 (m, C(6')CHMe), 1.07 (t, J=7.5, MeCH$_2$), 0.83 (d, J=7.1, MeC(2')).

$^{13}$C-NMR (100 MHz, $CDCl_3$): δ201.58 (s, CO), 141.80 (d, C(3)), 132.07 (d, C(2)), 131.38 (d, C(3')), 125.03 (d, C(4')), 52.29 (d, C(1')), 31.21 (d, C(2')), 30.11 (d, C(6')), 29.73 (t, C(5')), 26.16 (t, CH$_2$Me)), 18.05 (q, C(4)), 16.82 (q, MeC(2')), 10.49 (q, CH$_2$Me).

MS (EI): 192 (6), 177 (6), 163 (19), 149 (3), 145 (3), 137 (6), 123 (18), 108 (26), 93 (26), 91 (10), 81 (35), 79 (16), 77 (12), 69 (100), 55 (17), 41 (37), 39 (17).

IR: $ν_{max}$ 3020, 2964, 2914, 2875, 1694, 1665, 1629, 1443, 1375, 1290, 1217, 1197, 1172, 1136, 1117, 1092, 1048, 970, 902, 714 cm$^{-1}$.

Odour description: damascone-like, woody, agrestic, spicy.

EXAMPLE 2

(2E)-1-(rel-(1S,2S,6S)-6-Ethyl-2-methylcyclohex-3-enyl)but-2-en-1-one

A) At 20° C., sodium (0.11 g, 4.8 mmol) was added to ethanol (80 ml) and the resulting solution was treated with 1-(rel-(1R,2S,6S)-6-ethyl-2-methylcyclohex-3-enyl)ethan-1-one (8.6 g, 48 mmol). After refluxing 26 h, the resulting yellow solution was cooled, poured into ice-cooled water (1 l) and the aqueous phase was extracted with methyl tert.-butyl ether. The combined organic phases were washed with water then with a saturated aqueous NaCl solution, dried ($MgSO_4$), and concentrated. The crude product (8.15 g) consisted in a 70:26:4 mixture of 1-(rel-(1S,2S,6S)-/1-(rel-(1R,2S,6S)-6-ethyl-2-methylcyclohex-3-enyl)ethan-1-one/unassigned stereoisomer.

Data of 1-(rel-(1S,2S,6S)-6-ethyl-2-methylcyclohex-3-enyl)ethan-1-one:

$^1$H-NMR (400 MHz, $CDCl_3$): δ5.55 (dquint, J=2.3, 9.9, H—C(3'/4')), 5.49 (dsext, J=1.1, 10.1, H—C(4'/3'), 2.59-2.48

(m, H—C(2')), 2.46 (dd, J=3.2, 8.7, H—C(1')), 2.25-2.15 (m, H—C(5')), 2.17 (s, MeCO), 2.13-2.04 (m, H—C(5')), 1.98-1.89 (m, H—C(6')), 1.33-1.13 (m, $CH_2Me$), 0.94 (d, J=6.8, MeC(2')), 0.87 (t, J=7.5, $MeCH_2$).

$^{13}$C-NMR (100 MHz, $CDCl_3$): δ210.70 (s, CO), 131.96 (d, C(3')), 123.35 (d, C(4')), 58.60 (d, C(1')), 35.74 (d, C(2')), 29.70 (q, C(2)), 28.54 (t, C(5')), 27.85 (d, C(6')), 21.15 (t, $CH_2Me$), 20.60 (q, MeC(2')), 12.56 (q, $CH_2Me$).

B) At −78° C., a solution of n-butyl lithium (37.3 ml, 1.6M in hexane, 59 mmol) was treated with a solution of diisopropylamine (5.8 g, 57 mmol) in tetrahydrofuran (35 ml). The resulting solution was warmed to −20° C., cooled to −78° C., and treated with a solution of the crude 1-(6-ethyl-2-methyl-cyclohex-3-enyl)ethan-1-one mixture (8.1 g) in tetrahydrofuran (40 ml). The resulting solution was stirred 1 h at −70° C., warmed to 0° C., cooled at −70° C. and treated with a solution of acetaldehyde (10.5 g, 239 mmol) in tetrahydrofuran (40 ml). After 1 h stirring, a mixture of aqueous 2N HCl (50 ml) and saturated aqueous NaCl solution (50 ml) was added and the reaction mixture warmed to 0° C. The aq. phase was extracted with diethyl ether (2×100 ml) and the combined org. phases washed with saturated aqueous $NaHCO_3$ solution and water, dried ($MgSO_4$), and concentrated. The residue (13.4 g) dissolved in toluene (50 ml) was treated with para-toluene sulfonic acid monohydrate (0.5 g, 2.6 mmol) and refluxed during 1 h. The reaction mixture was cooled, treated with a saturated aqueous solution of $Na_2CO_3$ and the aqueous phase was extracted with cyclohexane (90 ml). The combined organic phases were washed with saturated aqueous NaCl solution, dried ($MgSO_4$) and concentrated. FC ($SiO_2$, hexane/methyl tert.-butyl ether 20:1) of the crude product gave (2E)-1-(rel-(1S,2S,6S)-6-ethyl-2-methylcyclohex-3-enyl)but-2-en-1-one (0.7 g, 3 steps: 7%) and a 67:27:6 mixture of (2E)-1-(rel-(1S,2S,6S)-/(2E)-1-(rel-(1R,2S,6S)-6-ethyl-2-methylcyclohex-3-enyl)but-2-en-1-one/unassigned stereoisomer (5.7 g, 3 steps: 58%).

Boiling point: 72° C. (0.1 mbar).

$^1$H-NMR (400 MHz, $C_6D_6$): δ6.79 (dq, J=6.9, 15.6, H—C(3)), 6.07 (dq, J=1.7, 15.5, H—C(2)), 5.63-5.55 (m, H—C(3'), H—C(4')), 2.96-2.86 (m, H—C(2')), 2.54 (dd, J=3.0, 9.1, H—C(1')), 2.16-2.03 (m, 2H, H—C(5')), 1.89-1.81 (m, H—C(6')), 1.55-1.35 (m, $CH_2Me$), 1.46 (dd, J=1.6, 7.0, MeC(3)), 1.07 (d, J=6.8, MeC(2')), 0.83 (t, J=7.5, $MeCH_2$).

$^{13}$C-NMR (100 MHz, $C_6D_6$): δ199.31 (s, CO), 140.69 (d, C(3)), 132.36 (d, C(3')), 131.10 (d, C(2)), 123.22 (d, C(4')), 55.82 (d, C(1')), 35.95 (d, C(6')), 28.53 (t, C(5')), 27.82 (d, C(2')), 20.71 (t, $CH_2Me$), 20.33 (q, MeC(2')), 17.36 (q, C(4)), 12.35 (q, $CH_2Me$).

MS (EI): 192 (6), 177 (4), 163 (7), 145 (2), 135 (4), 123 (12), 109 (6), 93 (21), 91 (11), 81 (32), 79 (18), 77 (16), 69 (100), 55 (11), 41 (29), 39 (15).

Odour description: fruity, damascone-like, dry fig, agrestic, green, sweet.

EXAMPLE 3

(2E)-1-(rel-(1R,2S,6S)-2-Ethyl-6-methylcyclohex-3-enyl)but-2-en-1-one

A) (2E)-1-(rel-(1R,2S,6S)-2-Ethyl-6-methylcyclohex-3-enyl)ethan-1-one (6.28 g, 92%) was prepared as described in Example 1 starting from 1,3-hexadiene (10 g, 0.122 mol, mixture of isomers) and 3-penten-2-one (5.7 g, 60% pure, 0.04 mol).

$^1$H-NMR (400 MHz, $CDCl_3$): δ5.80 (m, J=1.8, 2.3, 4.5, 10.1, 1H), 5.65 (m, J=1.5, 2.8, 4.3, 10.1, 1H), 2.62 (dd, J=5.3, 10.1, H—C(1')), 2.36-2.28 (m, 1H), 2.21-2.12 (m, 1H), 2.15 (s, MeC(3)), 2.11-2.01 (m, 1H), 1.65 (ddq, J=2.5, 9.1, 17.9, 1H), 1.35-1.20 (m, 2H), 0.93 (d, J=6.3, MeC(6')), 0.90 (t, J=7.3, $MeCH_2$).

$^{13}$C-NMR (100 MHz, $CDCl_3$): δ210.67 (s, CO), 128.94 (d), 125.98 (d), 57.63 (d), 37.28 (d), 33.19 (t), 30.64 (q), 25.12 (d), 24.96 (t), 20.30 (q), 11.98 (q).

MS (EI): 166 (17), 151 (11), 137 (20), 123 (55), 109 (11), 95 (16), 94 (7), 93 (34), 91 (9), 85 (58), 82 (23), 81 (70), 79 (26), 77 (21), 67 (30), 55 (19), 43 (100), 41 (18), 39 (12).

B) As described in Example 1, (2E)-1-(rel-(1R,2S,6S)-2-ethyl-6-methylcyclohex-3-enyl)but-2-en-1-one (1.75 g, 49%) was prepared from (2E)-1-(rel-(1R,2S,6S)-2-ethyl-6-methylcyclohex-3-enyl)ethan-1-one (3.1 g, 18.6 mmol) by aldolisation (LDA, AcH, THF) and water-elimination ($PTSA.H_2O$, cyclohexane, reflux, 1 h).

Boiling point: 90° C. (0.12 mbar).

$^1$H-NMR (400 MHz, $CDCl_3$): δ6.87 (dq, J=6.8, 15.7, H—C(3)), 6.17 (dq, J=1.7, 15.6, H—C(2)), 5.83-5.77 (m, 1H), 5.69-5.64 (m, 1H), 2.78 (dd, J=5.3, 10.1, H—C(1')), 2.30-2.23 (m, 1H), 2.23-2.06 (m, 2H), 1.90 (dd, J=1.8, 6.8, MeC(3)), 1.72-1.62 (m, 1H), 1.32-1.18 (m, 2H), 0.92 (d, J=6.1, MeC(6')), 0.86 (t, J=7.5, $MeCH_2$).

$^{13}$C-NMR (100 MHz, $CDCl_3$): δ201.62 (s, CO), 141.87 (d), 132.15 (d), 129.22 (d), 125.95 (d), 54.57 (d), 37.73 (d), 33.31 (t), 25.14 (d), 24.88 (t), 20.30 (q), 18.18 (q), 11.96 (q).

MS (EI): 192 (3), 177 (3), 163 (9), 149 (2), 145 (1), 137 (3), 123 (12), 111 (100), 93 (14), 91 (9), 81 (32), 79 (17), 77 (13), 69 (95), 55 (16), 41 (44), 39 (19).

IR: $\nu_{max}$ 3024, 2960, 2930, 2912, 2871, 2830, 1693, 1664, 1629, 1442, 1377, 1299, 1246, 1214, 1172, 1138, 1052, 968, 920, 889, 794, 707 $cm^{-1}$.

Odour description: fruity, red fruits, floral, rosy, damascone-like, agrestic, myrtle, armoise absolute.

EXAMPLE 4

(2E)-1-(rel-(1S,2S,6S)-2-Ethyl-6-methylcyclohex-3-enyl)but-2-en-1-one

A crude 80:20 mixture of 1-(rel-(1S,2S,6S)-/1-(rel-(1R,2S,6S)-2-ethyl-6-methylcyclohex-3-enyl)ethan-1-one (2.6 g) was prepared as described in Example 2 by EtONa catalyzed epimerization of 1-(rel-(1R,2S,6S)-2-ethyl-6-methylcyclohex-3-enyl)ethan-1-one (3.15 g, 18.9 mmol, Example 3) in ethanol (30 ml) at reflux (25 h). Aldolisation (LDA, AcH, THF) and water-elimination ($PTSA.H_2O$, cyclohexane, reflux, 45 min.) gave a 83:17 mixture of 1-(rel-(1S,2S,6S)-/1-(rel-(1R,2S,6S)-2-ethyl-6-methylcyclohex-3-enyl)ethan-1-one (1.27 g, 2 steps: 42%).

Boiling point (diastereomeric mixture): 72° C. (0.11 mbar).

Odour description (diast. mixt.): fruity, damascone-like, minty, agrestic.

A) 1-(rel-(1S,2S,6S)-2-Ethyl-6-methylcyclohex-3-enyl)ethan-1-one $^1$H-NMR (400 MHz, $CDCl_3$): δ5.65-5.56 (m, 2H), 2.56 (dd, J=3.1, 9.0, H—C(1')), 2.47-2.39 (m, 1H), 2.36-2.28 (m, 1H), 2.28-2.19 (m, 1H), 2.16 (s, MeCO), 1.94-1.86 (m, 1H), 1.46-1.34 (m, 1H), 1.27-1.14 (m, 1H), 0.90 (t, J=7.3, $MeCH_2$), 0.84 (d, J=7.3, MeC(6')).

¹³C-NMR (100 MHz, CDCl₃): δ210.75 (s, CO), 129.08 (d), 123.86 (d), 55.77 (d), 33.46 (d), 32.75 (t), 29.73 (q, MeCO), 28.26 (d), 27.00 (t), 14.99 (q), 10.88 (q).

MS (EI): 166 (21), 151 (2), 137 (17), 123 (82), 109 (7), 107 (8), 95 (29), 94 (9), 93 (35), 91 (21), 81 (56), 79 (30), 77 (13), 67 (17), 55 (19), 43 (100), 41 (21), 39 (19).

B) (2E)-1-(rel-(1S,2S,6S)-2-Ethyl-6-methylcyclohex-3-enyl)but-2-en-1-one

¹H-NMR (400 MHz, CDCl₃): δ6.87 (dq, J=6.9, 15.6, H—C(3)), 6.20 (dq, J=1.7, 15.6, H—C(2)), 5.66-5.58 (m, 2H), 2.72 (dd, J=3.2, 9.2, H—C(1')), 2.55-2.46 (m, 1H), 2.37-2.28 (m, 1H), 2.23-2.14 (m, 1H), 1.94-1.85 (m, 1H), 1.90 (dd, J=1.8, 6.8, MeC(3)), 1.45-1.34 (m, 1H), 1.26-1.13 (m, 1H), 0.89 (t, J=7.5, MeCH₂), 0.83 (d, J=7.1, MeC(6')).

¹³C-NMR (100 MHz, CDCl₃): δ201.62 (s, CO), 141.87 (d), 131.44 (d), 129.40 (d), 123.93 (d), 52.88 (d), 33.40 (d), 32.79 (t), 28.58 (d), 26.93 (t), 18.15 (q), 14.82 (q), 10.93 (q).

MS (EI): 192 (8), 177 (5), 163 (11), 149 (3), 145 (2), 137 (2), 123 (14), 111 (3), 108 (3), 93 (13), 91 (8), 81 (25), 79 (14), 77 (10), 69 (100), 55 (12), 41 (31), 39 (14).

IR: ν$_{max}$ 3021, 2961, 2909, 2875, 2837, 1693, 1664, 1629, 1442, 1379, 1341, 1286, 1212, 1179, 1142, 1122, 1088, 1050, 968, 901, 810, 688 cm⁻¹.

EXAMPLE 5

(2E)-1-(rel-(1S,6S)-6-Ethyl-cyclohex-3-enyl)but-2-en-1-one

As described in Example 1, 1-(rel-(1R,6S)-6-ethyl-cyclohex-3-enyl)ethan-1-one (5 g, 32%) was prepared starting from 1,3-butadiene (8.2 g, 151 mmol) and 3-hexen-2-one (9.9 g, 101 mmol) in toluene (56 ml) in the presence of BF₃.OEt₂ (3.6 g, 25 mmol) and was transformed by aldolisation (LDA, AcH, THF) and water-elimination (cat. PTSA.H₂O, toluene, 20° C., 15 h) into (2E)-1-(rel-(1S,6S)-6-ethyl-cyclohex-3-enyl)but-2-en-1-one (1.34 g, 23%, 12:88 diastereomeric mixture). 1-(rel-(1S,6S)-6-Ethyl-cyclohex-3-enyl)ethan-1-one (1.6 g, 32%) were recovered after FC.

A) 1-(rel-(1S,6S)-6-Ethyl-cyclohex-3-enyl)ethan-1-one

¹H-NMR (400 MHz, CDCl₃): δ5.71-5.63 (m, H—C(3'), H—C(4')), 2.72 (ddd, J=6.6, 8.3, 9.2, H—C(1')), 2.28-2.17 (m, 1H), 2.17-2.12 (m, 1H), 2.12 (s, MeCO), 1.90-1.79 (m, 1H), 1.76-1.66 (m, 1H), 1.51-1.40 (m, 1H), 1.24-1.12 (m, 1H), 0.90 (t, J=7.5, MeCH₂).

¹³C-NMR (100 MHz, CDCl₃): δ212.69 (s, CO), 125.98, 124.48 (2 d, C(3'), C(4')), 52.41 (d, C(1')), 36.12 (d, C(6')), 29.10 (t), 28.99 (q, C(2)), 27.37 (t), 26.49 (t), 10.84 (q, CH₂Me).

B) (2E)-1-(rel-(1S,6S)-6-Ethyl-cyclohex-3-enyl)but-2-en-1-one

Boiling point: 90° C. (0.5 mbar).
¹H-NMR (400 MHz, CDCl₃): main diast (1S,6S).: δ6.91 (dq, J=6.8, 15.7, H—C(3)), 6.23 (dq, J=1.7, 15.6, H—C(2)), 5.72-5.64 (m, H—C(3'), H—C(4')), 2.72 (dt, J=5.6, 9.6, H—C(1')), 2.24 (dm, J=18.2, H—C(2')), 2.19-2.13 (m, H—C(5')), 2.13-2.05 (dm, J=18.2, H—C(2')), 1.91 (dd, J=1.5, 6.8, MeC(3)), 1.92-1.82 (m, H—C(6')), 1.77-1.67 (m, H—C(5')), 1.51-1.40 (m, C(6')CHMe), 1.19-1.06 (m, C(6')CHMe), 0.87 (t, J=7.3, MeCH₂); minor diast. (1R,6S): δ6.89 (dq, J=6.8, 15.6, H—C(3)), 6.26 (dq, J=1.7, 15.5, H—C(2)), 5.70-5.58 (m, H—C(3'), H—C(4')), 2.91 (ddd, J=3.0, 5.6, 8.9, H—C(1')), 2.42-2.31 (m, 1H), 1.91 (dd, J=1.8, 6.8, MeC(3)), 0.86 (t, J=7.5, MeCH₂).

¹³C-NMR (100 MHz, CDCl₃): main diast.: δ203.88 (s, CO), 142.57 (d, C(3)), 131.21 (d, C(2)), 126.05 (d, C(3')), 124.93 (d, C(4')), 49.06 (d, C(1')), 36.37 (d, C(6')), 29.48 (t, C(5')), 28.36 (t, C(2')), 26.60 (t, CH₂Me), 18.15 (q, C(4)), 10.84 (q, CH₂Me); minor diast.: δ201.71 (s, CO), 141.77 (d, C(3)), 130.07 (d, C(2)), 125.32 (d, C(3')), 124.97 (d, C(4')), 47.87 (d, C(1')), 36.07 (d, C(6')), 31.47 (t, C(5')), 28.73 (t, C(2')), 26.79 (t, CH₂Me), 18.15 (q, C(4)), 12.29 (q, CH₂Me).

MS (EI): 178 (6), 163 (5), 149 (12), 145 (1), 137 (2), 135 (2), 131 (4), 121 (4), 109 (12), 108 (7), 95 (6), 94 (8), 93 (5), 91 (7), 81 (5), 79 (25), 77 (11), 69 (100), 67 (24), 55 (10), 41 (33), 39 (18).

IR: ν$_{max}$ 3026, 2963, 2913, 1691, 1666, 1627, 1438, 1377, 1294, 1218, 1177, 1130, 1080, 1060, 970, 937, 892, 660, 631 cm⁻¹.

Odour description: apple, rosy, damascone-like, fruity, spicy, woody.

EXAMPLE 6

(2E)-1-(1,2,5,6-Tetramethylcyclohex-3-enyl)but-2-en-1-one

As described in Example 1,1-(1,2,5,6-tetramethylcyclohex-3-enyl)ethan-1-one (0.9 g, 14%, 58:42 diastereomers mixture) was prepared starting from 2,4-hexadiene (3.5 g, 42.5 mmol) and 3-methyl-3-penten-2-one (3.4 g, 35 mmol) in toluene (17 ml) in the presence of BF₃.OEt₂ (1.2 g, 8.8 mmol) and a fraction (0.66 g, 3.7 mmol) was transformed by aldolisation (LDA, AcH, THF; FC) and water-elimination (cat. PTSA.H₂O, toluene, 20° C., 15 h) into (2E)-1-(1,2,5,6-tetramethylcyclohex-3-enyl)but-2-en-1-one (0.150 g, 20%, 57:43 diastereomeric mixture).

A) 1-(1,2,5,6-Tetramethylcyclohex-3-enyl)ethan-1-one

¹H-NMR (400 MHz, CDCl₃): main diast. δ5.56 (ddd, J=2.3, 5.3, 9.9, H—C(3'/4')), 5.41 (ddd, J=1.0, 2.0, 9.9, H—C(4'/3')), 2.34-2.21 (m, 1H), 2.14 (s, MeCO), 2.14-2.04 (m, 1H), 1.75-1.65 (m, 1H), 1.18 (s, MeC(1)), 1.04 (d, J=6.8, Me), 0.88 (d, J=6.3, Me), 0.80 (d, J=7.6, Me).

minor diast.: δ5.61 (dt, J=3.1, 10.0, H—C(3'/4')), 5.36 (dt, J=2.1, 10.0, H—C(4'/3')), 2.77-2.67 (m, 1H), 2.14-2.04 (m, 1H), 2.11 (s, MeCO), 1.82 (dq, J=6.3, 9.6, 1H), 0.95 (d, J=7.3, Me), 0.92 (s, MeC(1)), 0.84 (d, J=6.8, Me), 0.77 (d, J=7.1, Me).

B) (2E)-1-(1,2,5,6-Tetramethylcyclohex-3-enyl)but-2-en-1-one

Boiling point: 50° C. (0.15 mbar).
¹H-NMR (400 MHz, CDCl₃): main diast. δ6.93 (dq, J=6.9, 15.2, H—C(3)), 6.50 (dq, J=1.6, 15.1, H—C(2)), 5.57 (ddd, J=2.3, 5.3, 9.9, H—C(3'/4'), 5.42 (br. d, J=9.9, H—C(4'/3')), 2.35-2.24 (m, 1H), 2.14-2.04 (m, 1H), 1.89 (dd, J=1.8, 6.8, MeC(3)), 1.79-1.68 (m, 1H), 1.16 (s, MeC(1)), 1.06 (d, J=7.1, Me), 0.91 (d, J=6.3, Me), 0.78 (d, J=7.1, Me); minor diast.: δ6.97 (dq, J=6.8, 15.2, H—C(3)), 6.59 (dq, J=1.5, 14.9, H—C(2)), 5.61 (dt, J=3.3, 10.1, H—C(3'/4'), 5.38 (dt, J=2.0, 10.1, H—C(4'/3')), 2.78-2.68 (m, 1H), 2.14-2.04 (m, 1H), 1.89 (MeC(3)), 1.90-1.83 (m, 1H), 0.95 (d, J=7.3, Me), 0.93 (s, MeC(1)), 0.81 (d, J=6.8, Me), 0.77 (d, J=7.6, Me).

MS (EI): main diast.: 206 (3), 191 (3), 177 (4), 150 (3), 149 (4), 138 (11), 137 (100), 136 (27), 135 (70), 134 (12), 121 (38), 109 (22), 107 (19), 95 (79), 93 (14), 91 (23), 81 (29), 79 (16), 77 (16), 69 (55), 57 (27), 55 (22), 41 (59), 39 (26).

IR: ν$_{max}$ 3026, 2967, 2876, 1687, 1625, 1445, 1375, 1288, 1184, 1137, 1065, 1042, 967, 928, 860, 790, 750, 721, 643 cm$^{-1}$.

Odour description: fruity, damascone-like, mirabelle, dry fruits, cassis, minty.

EXAMPLE 7

(2E)-1-(1,2-Dimethylcyclohex-3-enyl)but-2-en-1-one

As described in Example 1, 1-(1,2-dimethylcyclohex-3-enyl)ethan-1-one (13 g, 66%) was prepared starting from 1,3-pentadiene (10.6 g, 156 mmol) and 3-methyl-3-buten-2-one (10.9 g, 130 mmol) in toluene (65 ml) in the presence of BF$_3$.OEt$_2$ (4.6 g, 32 mmol) and a fraction (7 g, 46 mmol) was transformed by aldolisation (LDA, AcH, THF; FC, 2.4 g starting material recovered) and water-elimination (cat. PTSA.H$_2$O, toluene, reflux, 2 h) into (2E)-1-(1,2-dimethylcyclohex-3-enyl)but-2-en-1-one (1.54 g, 2 steps: 19%).

A) 1-(1,2-Dimethylcyclohex-3-enyl)ethan-1-one

Boiling point: 100° C. (15 mbar).
$^1$H-NMR (400 MHz, CDCl$_3$): δ$^1$H-NMR (400 MHz, CDCl$_3$): δ5.64-5.55 (m, H—C(3'), H—C(4'), 2.26-2.18 (m, 1H), 2.14 (s, MeCO), 2.13-1.93 (m, 2H), 1.81 (ddd, J=6.6, 11.1, 13.6, 1H), 1.48 (ddm, J=6.2, 13.7, 1H), 1.16 (s, MeC(1)), 0.85 (d, J=7.1, Me).

MS (EI): 152 (6), 137 (3), 110 (9), 109 (100), 95 (2), 91 (11), 85 (5), 81 (23), 79 (13), 77 (13), 69 (5), 67 (63), 55 (15), 53 (11), 43 (48), 41 (19), 39 (15).

IR: ν$_{max}$ 3020, 2967, 1702, 1454, 1433, 1375, 1355, 1248, 1223, 1202, 1103, 1085, 1042, 972, 951, 865, 804, 756, 707, 657 cm$^{-1}$.

B) (2E)-1-(1,2-Dimethylcyclohex-3-enyl)but-2-en-1-one

Boiling point: 70° C. (15 mbar).
$^1$H-NMR (400 MHz, CDCl$_3$): δ$^1$H-NMR (400 MHz, CDCl$_3$): δ6.98 (dq, J=6.9, 15.2, H—C(3)), 6.50 (dq, J=1.7, 15.2, H—C(2)), 5.64-5.56 (m, H—C(3'), H—C(4'), 2.31-2.21 (m, 1H), 2.15-1.94 (m, 2H), 1.90 (dd, J=1.6, 6.9, MeC(3)), 1.79 (ddd, J=6.7, 10.8, 13.9, 1H), 1.55 (ddm, J=6.1, 13.9, 1H), 1.15 (s, MeC(1)), 0.84 (d, J=7.1, Me).

MS (EI): 178 (9), 163 (6), 149 (3), 137 (3), 123 (12), 110 (14), 109 (100), 93 (15), 91 (14), 81 (24), 79 (17), 77 (16), 69 (68), 67 (66), 55 (17), 53 (13), 43 (17), 41 (48), 39 (29).

IR: ν$_{max}$ 3019, 2966, 2874, 1691, 1628, 1454, 1444, 1375, 1320, 1289, 1188, 1054, 1027, 968, 932, 868, 842, 766, 749, 706 cm$^{-1}$.

Odour description: fruity, bilberry, cassis, agrestic, minty, damascone-like.

EXAMPLE 8

(2E)-1-(2,5-Dimethylcyclohex-3-enyl)but-2-en-1-one

As described in Example 1, 1-(2,5-dimethylcyclohex-3-enyl)ethan-1-one (6.4 g, 28%) was prepared starting from 2,4-hexadiene (15 g, 183 mmol) and methyl vinyl ketone (10.6 g, 152 mmol) in toluene (75 ml) in the presence of BF$_3$.OEt$_2$ (5.4 g, 38 mmol) and transformed by aldolisation (LDA, AcH, THF; FC) and water-elimination into (2E)-1-(2,5-dimethylcyclohex-3-enyl)but-2-en-1-one (2.3 g, 2 steps: 49%, 75:25 diastereomeric mixture).

A) 1-(2,5-dimethylcyclohex-3-enyl)ethan-1-one $^1$H-NMR (400 MHz, CDCl$_3$): δ5.64 (ddd, J=2.5, 4.8, 9.9, H—C(3'/4'), 5.48 (ddd, J=1.6, 3.2, 9.9, H—C(4'/3')), 2.76 (ddd, J=2.4, 5.4, 12.6, H—C(6')), 2.73-2.64 (m, 1H), 2.22-2.11 (m, 1H), 2.15 (s, MeCO), 1.78 (ddm, J=5.6, 13.4, 1H), 1.27 (ddd, J=11.1, 12.5, 13.5, 1H), 1.01 (d, J=7.1, Me), 0.82 (d, J=6.8, Me).

B) (2E)-1-(2,5-Simethylcyclohex-3-enyl)but-2-en-1-one $^1$H-NMR (400 MHz, CDCl$_3$): main diast.: δ6.91 (dq, J=6.8, 15.7, H—C(3)), 6.21 (dq, J=1.7, 15.6, H—C(2)), 5.58 (dddd, J=1.0, 2.0, 4.0, 9.9, H—C(3'/4'), 5.48 (dt, J=1.8, 10.0, H—C(4'/3')), 2.59-2.50 (m, 2H), 2.33-2.23 (m, 1H), 1.92 (dd, J=1.8, 6.8, MeC(3)), 1.76 (ddd, J=5.8, 11.1, 13.1, 1H), 1.56 (dddd, J=1.0, 2.8, 3.0, 13.4, 1H), 1.04 (d, J=7.1, Me), 0.92 (d, J=6.8, Me); minor diast.: δ6.90 (dq, J=6.9, 15.5, H—C(3)), 6.22 (dq, J=1.7, 15.7, H—C(2)), 5.63 (ddd, J=2.5, 4.8, 9.9, H—C(3'/4'), 5.49 (dt, J=1.7, 9.9, H—C(4'/3')), 2.96 (ddd, J=2.5, 5.6, 12.6, H—C(6')), 2.67-2.56 (m, 1H), 2.33-2.23 (m, 1H), 1.90 (dd, J=1.6, 6.9, MeC(3)), 1.79-1.70 (m, 1H), 1.35 (ddd, J=11.1, 12.6, 13.6, 1H), 1.02 (d, J=7.1, Me), 0.78 (d, J=7.1, Me)

$^{13}$C-NMR (100 MHz, CDCl$_3$): main diast.: δ202.98 (s, CO), 142.35 (d), 131.52 (d), 130.96 (d), 130.89 (d), 47.84 (d, C(1')), 32.43 (d), 31.39 (d), 28.53 (t, C(6')), 21.01 (q), 20.14 (q), 18.17 (q, C(4)); minor diast.: δ201.98 (s, CO), 141.94 (d), 132.73 (d), 130.92 (d), 130.21 (d), 48.44 (d, C(1')), 31.20 (d), 30.92 (d), 27.06 (t, C(6')), 21.53 (q), 18.12 (q, C(4)), 16.12 (q).

MS (EI): 178 (3), 163 (4), 149 (1), 145 (2), 135 (2), 123 (6), 109 (25), 108 (11), 93 (10), 91 (11), 81 (6), 79 (11), 77 (10), 69 (100), 67 (17), 65 (4), 55 (10), 41 (32), 39 (19).

IR: ν$_{max}$ 3013, 2957, 2929, 2871, 1694, 1667, 1630, 1443, 1374, 1289, 1225, 1198, 1181, 1150, 1128, 1087, 1050, 970, 919, 729 cm$^{-1}$.

Boiling point (diastereomeric mixture): 60° C. (0.1 mbar).

Odour description: fruity, damascone-like, dry fruit, plum, apple, agrestic.

EXAMPLE 9

The following compounds were prepared according to the general procedure of Example 1.

| Example | R¹ | R² | R³ | R⁴ | R⁵ | Odour description |
|---|---|---|---|---|---|---|
| 9a | CH₃ | CH₃ | H | H | C₂H₅ | fruity, agrestic, damascone-like, myrtle, aromatic |
| MS (EI): 206, 191, 177, 137, 125, 107, 95, 81, 69, 55, 41 | | | | | | |
| 9b | H | C₂H₅ | CH₃ | H | CH₃ | damascone-like, honey, terpenic |
| MS (EI): 206, 191, 177, 173, 163, 159, 151, 137, 122, 107, 95, 93, 81, 69, 55, 41 | | | | | | |
| 9c | H | C₂H₅ | H | CH₃ | CH₃ | plum, damascone-like, agrestic |
| MS (EI): 206, 191, 177, 173, 163, 159, 149, 137, 121, 109, 107, 95, 81, 69, 55, 41 | | | | | | |
| 9d | H | CH₃ | H | CH₃ | CH₃ | fruity, floral, damascone-like |
| MS (EI): 192, 177, 163, 159, 149, 137, 123, 107, 95, 91, 81, 69, 55, 41 | | | | | | |
| 9e | H | CH₃ | CH₃ | CH₃ | CH₃ | fruity, rosy, plum, damascone-like |
| MS (EI): 206, 191, 178, 173, 163, 158, 149, 137, 121, 107, 95, 81, 69, 55, 41 | | | | | | |
| 9f | H | CH₃ | CH₃ | H | CH₃ | fruity, floral, green, cassis, damascone-like |
| MS (EI): 192, 177, 163, 159, 149, 137, 123, 111, 95, 91, 81, 69, 55, 41 | | | | | | |
| 9g | CH₃ | H | H | CH₃ | CH₃ | fruity, floral, green, cassis, damascone-like |
| MS (EI): 192, 177, 163, 159, 149, 135, 123, 107, 95, 91, 81, 69, 55, 41 | | | | | | |
| 9h | CH₃ | H | CH₃ | CH₃ | CH₃ | fruity, rosy, green, cassis, damascone-like |
| MS (EI): 206, 191, 177, 173, 163, 137, 121, 109, 95, 81, 69, 57, 41 | | | | | | |
| 9i | CH₃ | CH₃ | H | CH₃ | CH₃ | damascone-like, fruity, rosy |
| MS (EI): 206, 191, 177, 173, 163, 150, 137, 125, 121, 109, 95, 81, 69, 57, 41 | | | | | | |
| 9j | H | H | H | CH₃ | CH₃ | damascone-like, fruity, rosy |
| MS (EI): 178, 163, 149, 145, 135, 121, 109, 97, 91, 79, 69, 55, 41 | | | | | | |
| 9k | H | H | CH₃ | CH₃ | CH₃ | damascone-like, fruity, rosy, agrestic |
| MS (EI): 192, 177, 163, 159, 149, 135, 123, 107, 96, 91, 81, 69, 67, 55, 41 | | | | | | |
| 9l | CH₃ | CH₃ | H | H | CH₃ | fruity, damascone-like, agrestic |
| MS (EI): 192, 177, 163, 159, 149, 137, 123, 107, 95, 91, 81, 69, 55, 41 | | | | | | |
| 9m | CH₃ | H | CH₃ | H | CH₃ | fruity, agrestic, blackcurrant, damascone-like |
| MS (EI): 192, 177, 164, 159, 149, 137, 123, 111, 107, 95, 91, 81, 69, 55, 41 | | | | | | |
| 9n | CH₃ | CH₃ | H | H | H | fruity, agrestic, damascone-like |
| MS (EI): 178, 163, 149, 145, 135, 123, 109, 93, 81, 77, 69, 55, 41 | | | | | | |

EXAMPLE 9

A Fragrance Composition for a Soap Having a Tea Aroma

| Compound/Ingredient | parts by weight 1/1270 |
|---|---|
| Evernyl (methyl 2,4-dihydroxy-3,6-dimethylbenzoate) | 1 |
| Undecavertol (4-methyl-3-decen-5-ol) | 1 |
| Citronnelle essential oil Java | 2 |
| Cyclal C (2,4-dimethyl-3-cyclohexene-1-carboxaldehyde) | 2 |
| Eucalyptus essential oil China | 2 |
| Lemonile ® (3,7-Dimethyl-2(3),6-nonadienenitriles) | 2 |
| 2-Isobutyl Quinoleine at 10% in DPG (dipropylene glycol) | 2 |
| Aldehyde C 12 MNA (2-methylundecanal) | 3 |
| Ambrofix (CAS 6790-58-5) at 10% in DPG (dipropylene glycol) | 3 |
| Freskomenthe ® (2-(1-methylpropyl) cyclohexanone) | 5 |
| Aldehyde C 110 Undecylic (undecanal) | 10 |
| Gaiacwood oil | 10 |
| Peach Pure (gamma-Undecalactone) | 10 |
| Geraniol | 20 |
| Hedione (Methyl dihydrojasmonate) | 32 |
| Beta Dihydro Ionone | 35 |
| Terpineol | 40 |
| Galaxolide ® 50 (1,3,4,6,7,8-hexahydro-4,6,6,7,8,8-hexamethyl-cyclopenta-gamma-2-benzopyran) at 50% in diethylphtalate | 70 |
| Beta Ionone | 70 |
| Hexyl Salicylate | 80 |
| Bergamote Givco 104* | 100 |
| Terpinyl acetate | 100 |
| Agrumex (2-tert.-butylcyclohexyl acetate) | 100 |
| Lemon essential oil Reconstitution 1385** | 100 |
| Verdyl Propionate | 100 |
| Alpha Hexyl Cinnamic Aldehyde | 150 |

-continued

| Compound/Ingredient | parts by weight 1/1270 |
|---|---|
| Linalool | 200 |
| Butenone of Example 1 at 10% in DPG | 20 |

*Base available form Givaudan SA (see Fragrance Ingredients Index 2004)
**Origin: Givaudan SA, Switzerland The butenone of Example 1 underlines the fruity aspect of the tea-notes and their honey facet. The accord is cleaner, has less of a cork-aspect than in the case δ-damascone is used.

The invention claimed is:

1. A compound of formula (I)

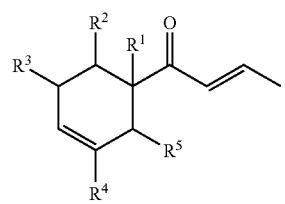

(I)

wherein
the double bound in the side chain is in E-configuration;
R¹, R², R³, R⁴ and R⁵ are independently selected from hydrogen, methyl or ethyl; and
the total sum of carbon atoms is 11 to 15;
with the proviso that
if R² is hydrogen then R⁵ is methyl or ethyl;
if R⁵ is hydrogen then R² is methyl or ethyl; and
if R⁴ is methyl or ethyl then R⁵ is methyl or ethyl.

2. A compound according to claim 1 wherein
$R^1$ is hydrogen, methyl or ethyl,
$R^2$ is methyl or ethyl, and
$R^3$, $R^4$ and $R^5$ are hydrogen.

3. A compound according to claim 1 wherein
$R^1$ and $R^2$ are independently selected from hydrogen, methyl or ethyl,
$R^3$ and $R^4$ are hydrogen, and
$R^5$ is methyl or ethyl.

4. A compound according to claim 1 wherein
$R^1$ is selected from hydrogen, methyl or ethyl,
$R^2$ is methyl or ethyl,
$R^3$ is methyl or ethyl, and
$R^4$ and $R^5$ are hydrogen.

5. A compound according to claim 1 wherein
$R^1$ and $R^2$ are independently selected from hydrogen, methyl or ethyl,
$R^4$ and $R^5$ are independently selected from methyl or ethyl, and
$R^3$ is hydrogen.

6. A compound according to claim 1 wherein
$R^1$ and $R^2$ are independently selected from hydrogen, methyl or ethyl,
$R^4$ is hydrogen, and
$R^3$ and $R^5$ are independently selected from methyl or ethyl.

7. A compound according to claim 1 wherein
$R^1$ and $R^2$ are independently selected from hydrogen, methyl or ethyl, and
$R^3$, $R^4$ and $R^5$ are independently selected from methyl or ethyl.

8. A compound according to claim 1 selected from
(2E)-1-(6-ethyl-2-methylcyclohex-3-enyl)but-2-en-1-one,
(2E)-1-(2-ethyl-6-methylcyclohex-3-enyl)but-2-en-1-one,
(2E)-1-(6-ethylcyclohex-3-enyl)but-2-en-1-one,
(2E)-1-(1,2,5,6-tetramethylcyclohex-3-enyl)but-2-en-1-one,
(2E)-1-(1,2-dimethylcyclohex-3-enyl)but-2-en-1-one,
(2E)-1-(2,5-dimethylcyclohex-3-enyl)but-2-en-1-one,
(2E)-1-(1,6-dimethyl-2-ethylcyclohex-3-enyl)but-2-en-1-one,
(2E)-1-(2,5-dimethyl-6-ethylcyclohex-3-enyl)but-2-en-1-one,
(2E)-1-(2,3-dimethyl-6-ethylcyclohex-3-enyl)but-2-en-1-one,
(2E)-1-(2,3,6-trimethylcyclohex-3-enyl)but-2-en-1-one,
(2E)-1-(2,3,5,6-tetramethylcyclohex-3-enyl)but-2-en-1-one,
(2E)-1-(2,5,6-trimethylcyclohex-3-enyl)but-2-en-1-one,
(2E)-1-(1,2,3-trimethylcyclohex-3-enyl)but-2-en-1-one,
(2E)-1-(1,2,3,5-tetramethylcyclohex-3-enyl)but-2-en-1-one,
(2E)-1-(1,2,3,6-tetramethylcyclohex-3-enyl)but-2-en-1-one,
(2E)-1-(2,3-dimethylcyclohex-3-enyl)but-2-en-1-one,
(2E)-1-(2,3,5-trimethylcyclohex-3-enyl)but-2-en-1-one,
(2E)-1-(1,2,6-trimethylcyclohex-3-enyl)but-2-en-1-one,
(2E)-1-(1,2,5-trimethylcyclohex-3-enyl)but-2-en-1-one, and
(2E)-1-(1,6-dimethylcyclohex-3-enyl)buten-1-one.

9. A compound according to claim 1 wherein at least one of the residues $R^2$, $R^3$, $R^4$ and $R^5$ is ethyl.

10. A flavour or fragrance composition comprising a compound of formula (I) according to claim 1.

11. A fragrance application comprising
a) a compound of formula (I) according to claim 1 and
b) a consumer product base.

12. A fragrance application according to claim 11 wherein the consumer product base is selected from the group consisting of fine fragrance, household product, laundry product, body care product and cosmetic.

13. A method of manufacturing a flavour or fragrance composition, comprising the step of incorporating an effective amount of a compound of formula (I) according to claim 1 to a base material.

14. A method of improving, enhancing or modifying a fragrance of a fragrance composition or fragrance application comprising incorporating an effective amount of a compound of formula (I) according to claim 1 to a base material.

15. A flavour or fragrance ingredient comprising a compound of formula (I) according to claim 1.

* * * * *